(12) United States Patent
Mihaila et al.

(10) Patent No.: US 9,097,741 B2
(45) Date of Patent: Aug. 4, 2015

(54) MOLECULE SENSING AND IDENTIFICATION

(71) Applicant: Honeywell International Inc., Morristown, NJ (US)

(72) Inventors: Mihai N. Mihaila, Bucharest (RO); Bogdan Serban, Bucharest (RO)

(73) Assignee: Honeywell International Inc., Morristown, NJ (US)

( * ) Notice: Subject to any disclaimer, the term of this patent is extended or adjusted under 35 U.S.C. 154(b) by 189 days.

(21) Appl. No.: 13/767,611

(22) Filed: Feb. 14, 2013

(65) Prior Publication Data
US 2013/0335060 A1 Dec. 19, 2013

(30) Foreign Application Priority Data

Feb. 14, 2012 (EP) .................................. 12155445

(51) Int. Cl.
*G01R 19/00* (2006.01)
*G01N 27/414* (2006.01)

(52) U.S. Cl.
CPC .............. *G01R 19/00* (2013.01); *G01N 27/414* (2013.01)

(58) Field of Classification Search
CPC ................... H05H 1/0081; H05H 2001/2412; H05H 3/02; H05H 2001/2418; G01N 2021/458; G01N 27/227; G01N 21/31
USPC .................... 324/76.11, 693, 71.1, 74, 750.3, 324/756.01; 257/E21.578, E29.168, 383
See application file for complete search history.

(56) References Cited

U.S. PATENT DOCUMENTS

| 6,202,471 | B1 | 3/2001 | Yadav et al. |
| 7,547,881 | B2 * | 6/2009 | Hunt et al. .................... 250/305 |
| 2008/0119366 | A1 * | 5/2008 | Sauer et al. ....................... 506/7 |
| 2009/0014757 | A1 * | 1/2009 | Takulapalli et al. .......... 257/253 |
| 2009/0072137 | A1 | 3/2009 | Hunt et al. |
| 2010/0126885 | A1 * | 5/2010 | Iechi et al. .................... 205/793 |

OTHER PUBLICATIONS

A Search Report from related European Application No. 12155445.5, dated Jun. 6, 2012, 4 pgs.
Fujita, et al. "Topological Insulator Cell for Memory and Magnetic Sensor Applications", Appl. Phys. Express, vol. 4, (XP 002676810), 3 pgs., published online Sep. 7, 2011.
Joel E. Moore, The birth of topological insulators, Nature 464, 194, Mar. 2010 (5 pages).
Kane, et al., Topological insulators, Physics World, Feb. 2011 (5 pages).
D. Hsieh, et al, Observation of Unconventional Quantum Spin Textures in Topological Insulators, Science 323, 919, Feb. 2009 (4 pages).
D. Hsieh, et al., A topological Dirac insulator in a quantum spin Hall phase, Nature 454, 970, 2008 (4 pages).

(Continued)

*Primary Examiner* — Melissa Koval
*Assistant Examiner* — Nasima Monsur
(74) *Attorney, Agent, or Firm* — Brooks, Cameron & Huebsch, PLLC

(57) ABSTRACT

The present disclosure includes devices and methods for spectroscopic identification of molecules. One device includes a topological insulator layer oriented either above or below two metallic contacts and wherein the contacts are oriented such that a voltage can be applied across the contacts and a current-voltage characteristic can be measured.

18 Claims, 2 Drawing Sheets

(56) References Cited

OTHER PUBLICATIONS

M. Zahid Hasan, et al., Colloquium: Topological Insulators, Reviews of Modern Physics, vol. 82, pp. 3045-3067 (24 pages), Nov. 8, 2010.

Y.L. Chen, et al., Experimental Realization of a Three-Dimensional Topological Insulator, Bi2Te3, Science 325, 178, Jul. 2009 (4 pages).

* cited by examiner

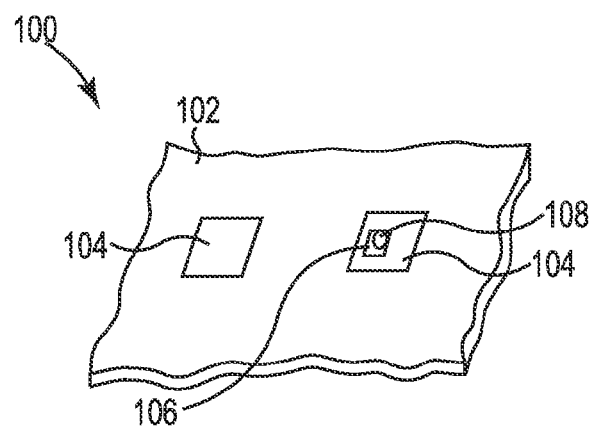
*Fig. 1*
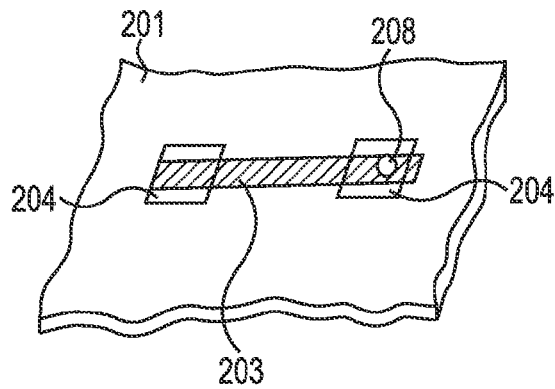
*Fig. 2*
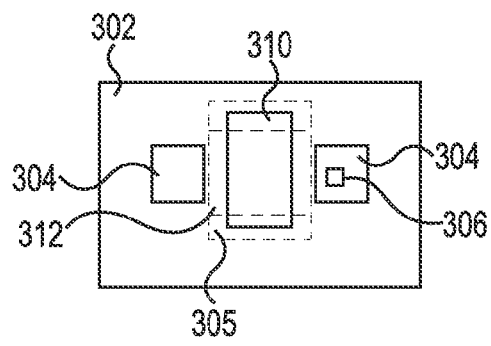 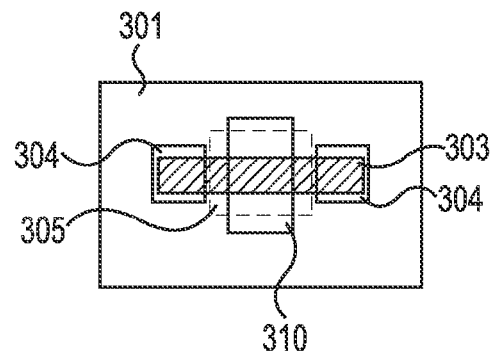
*Fig. 3a*   *Fig. 3b*

MOLECULE SENSING AND IDENTIFICATION

CROSS REFERENCE TO RELATED APPLICATIONS

The present application claims foreign priority to EP Application No. 12155445.5, filed Feb. 14, 2012, the disclosure of which is herein incorporated by reference.

TECHNICAL FIELD

The present disclosure relates to molecule sensors and devices and methods for sensing and identifying molecules.

BACKGROUND

Molecule sensing and identification devices (generally referred to as molecule sensors herein) can be utilized in many fields of technology. In the production of molecule sensing and identification devices, issues may arise with respect to the materials chosen to create the devices.

For example, a material, such as graphene, may have excellent sensing capabilities when tested in lab conditions, but the material may not be suitable for use in fabricating a device. For instance, the material may be difficult to manipulate into a layer used to form a portion of the device and/or may be irregular in its structure and/or sensing quality and therefore may not produce a suitable molecule sensing device once manufactured.

BRIEF DESCRIPTION OF THE DRAWINGS

FIG. 1 illustrates an embodiment of a molecule sensor constructed in accordance with one or more embodiments of the present disclosure.

FIG. 2 illustrates another embodiment of a molecule sensor constructed in accordance with one or more embodiments of the present disclosure.

FIG. 3a illustrates another embodiment of a molecule sensor constructed in accordance with one or more embodiments of the present disclosure.

FIG. 3b illustrates another embodiment of a molecule sensor constructed in accordance with one or more embodiments of the present disclosure.

DETAILED DESCRIPTION

Figure 4A:
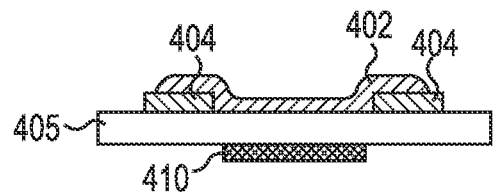
FIGS. 4a and 4b illustrate a side view of two embodiments of a molecule sensor constructed in accordance with one or more embodiments of the present disclosure.

The embodiments of the present disclosure utilize topological insulators to provide molecule sensing and identification devices (i.e., molecule sensors) and methods. Such sensors may be capable, for example, of sensing and/or identifying any molecule and can be particularly useful for sensing and/or identifying gas molecules.

One such device embodiment includes a topological insulator oriented either above or below two metallic contacts and wherein the contacts are oriented such that a voltage can be applied across the contacts and a current-voltage characteristic can be identified. An irregularity, such as a non-linearity, can occur in I(V) when molecules exist on the topological insulator. This can be utilized as a beneficial technique particularly, when the system is linear (e.g., an Ohmic system). The design of such embodiments may enable the device to sense and/or identify any type of molecule and, in some embodiments, a combination of multiple and/or mixed molecules.

Topological insulators are materials that conduct only at the surface, with the bulk of the material being an insulator. Examples of such materials include, but are not limited to, $Bi_2Se_3$ (i.e., Guanajuatite) and $Bi_2Te_3$ (i.e., Bismuth Telluride).

One benefit of using a topological insulating material is that the materials seem to be easier to prepare from a manufacturing standpoint and therefore can more readily be made into devices than previous materials, such as graphene.

Additionally, these materials may be easier to manipulate than previous materials. For example, if a film of topological insulator material is used to fabricate a device, masking can, for instance, be utilized to create different shapes (e.g., stripes, crosses, etc).

In some implementations, if the topological insulator is placed on an insulator (e.g., silicon dioxide) it may not effect the conduction of the electrons as readily as prior materials. Further, the bonding between a topological insulator and an insulator may be better than with prior materials.

With regard to ballistic movement, the electron mobility in the surface atomic layer of such topological insulator materials can be of the order 10,000 $cm^2/Vs$. Therefore, between two close contacts on the surface of such materials, electrons may be able to move ballistically, with little or no scattering.

Such movement can, for example, be accomplished by applying a voltage to two or more metallic regions (e.g., contacts) of a ballistic structure sufficient to generate ballistic electron flow. One or more molecules to be sensed and/or identified can be placed in contact with or can contact one or more ballistic electrons in a manner sufficient to excite at least one vibration mode of the one or more molecules.

The change in an electronic property of the ballistic structure (e.g., current-voltage characteristic), in response to the excitation of at least one vibration mode, can be measured. From this information, spectral data from the measured change, sufficient to provide sensing and/or identification information of the one or more molecules, can be generated.

The embodiments of the present disclosure can rely on the use of these ballistic electron movements to reveal a vibration spectrum of molecules. The identification of a vibration by the device can be used as a mechanism to sense the existence of a molecule. Additionally, each molecule has a unique vibration and, therefore, the vibration of the molecule can be useful in identifying the type of molecule or a mix of molecules being sensed, in some embodiments.

For example, these ballistic electrons can excite the specific vibration modes of a given molecule if the molecule is located close to the electrode where the ballistic electrons acquire the energy eV, where e is the elementary charge and V is the applied voltage across the ballistic structure. If the energy eV of the ballistic electrons corresponds to a vibration mode of the molecule, the electron energy eV is resonantly transferred to the molecule.

The vibration of the molecule modulates the conductivity of the molecular system, therefore, the molecule vibration can be detected by monitoring the value of the current (I) flowing in the system as a function of the applied voltage (V) (i.e., current-voltage characteristic) across the sensor terminals. The vibration spectrum of the molecule manifests as a fine structure in the I(V) or in the conductance (i.e., I(V) first derivative) or its first derivative (i.e., I(V) second derivative).

In some embodiments, depending on the value of V, one can detect a single molecular vibration mode. The whole vibration spectrum of the molecule can be observed by sweeping a voltage across the sensor contacts. In this respect, the sensor can act as a spectrometer (e.g., a nanospectrometer).

In such embodiments, the molecule can, for example, be identified from its unique vibration spectrum. In various embodiments, molecules of the same type, mixed molecules together, multiple different molecules in succession, and/or a single molecule can be sensed using such techniques.

In order to detect the spectrum of the molecule, one can register the I(V) characteristic of the system. For example, a structure composed of peaks and dips, located at voltages corresponding to the energies of the molecular vibration modes, can be evident in the I(V) characteristics.

A higher resolution can be achieved, in some embodiments, by calculating the first, $dI/dV$, and the second derivative, $d^2I/dV^2$. In such an analysis, a structure composed of peaks and dips can be evident in $dI/dV$ and $d^2I/dV^2$, at voltages corresponding to the vibration energies of the molecule.

FIG. 1 illustrates an embodiment of a molecule sensor constructed in accordance with one or more embodiments of the present disclosure. In the embodiment of FIG. 1, contacts 104 (e.g. ohmic contacts of titanium and/or gold (Ti/Au)) can be deposited on a topological insulator surface 102 of the device 100. If the contacts are positioned close enough to each other, ballistic electrons may start flowing when an appropriate biasing voltage is applied to the structure.

For example, FIG. 1 illustrates a device 100 for spectroscopic identification of one or more molecules 108. The device 100 includes a topological insulator layer 102. The topological insulator can be oriented below the two metallic contacts 104, as shown in FIG. 1, and the contacts can be oriented such that a voltage can be applied across the contacts and a current-voltage characteristic can be measured.

Such a structure can be provided via a method wherein the method includes providing a topological insulator layer oriented either above or below two metallic contacts and wherein the contacts are oriented such that a voltage can be applied across the contacts and a current-voltage characteristic can be measured.

Depending on the distance between the contacts and the biasing voltage, the system can be in the ballistic transport regime (i.e., the electrons can travel freely from one electrode to another). If a molecule (e.g., molecule 108) is placed, intentionally or not, at one of the contacts 104, the ballistic electrons can excite the vibration modes of the molecule when it's energy eV equals the energy of a molecular vibration mode.

In some embodiments, such as that illustrated in FIG. 1, a hole 106 can be positioned in one of the contacts 104 to allow absorption of the molecule 108 on the topological insulator 102. In various embodiments, a protective material can be used to cover the topological insulator 102 between the contacts 104, so as to reduce or avoid absorption of the molecule 108 between the contacts 104.

FIG. 2 illustrates another embodiment of a molecule sensor constructed in accordance with one or more embodiments of the present disclosure. FIG. 2 illustrates a device embodiment for sensing and/or identifying one or more molecules 208. in this embodiment, the topological insulator 203 is formed between the two contacts 204.

In the embodiment illustrated in FIG. 2, the topological insulator 203 is also formed over at least a portion of the contacts 204. In some embodiments, the topological insulator can formed between the contacts, but not over the contacts or can be formed over a portion, but not all of one or both of the contacts.

As discussed above, in the embodiment of FIG. 2, the contacts are deposited on the surface of an insulator (e.g.: SiO2), separated by a distance, for example, of a few microns. Then, a topological insulator (e.g.: $Bi_2Se_3$, $Bi_2Te_3$, among others), for example, in form of a film strip, ribbon, or wire (e.g., nanostrip, nanoribbon, nanowire) can be deposited between metallic contacts.

In some embodiments, an insulating layer is formed on the topological insulator. An insulating layer can, for example, be provided by a high k dielectric material, such as SiO2 as discussed above. In some such embodiments, a gate contact can be formed on the insulating layer. For example, a gate contact can be formed wherein the positioning of the layers is gate/insulator/thermal insulator or thermal insulator/insulator/gate. A gate contact can, for example, be provided by a metallic or doped poly-silicon material in various embodiments.

In another embodiment, the structures in the FIGS. 1 and 2 can be provided with a gate contact located above the topological insulator and between the contacts. To this purpose, an insulator layer can be deposited on the topological insulator, then the gate contact can be formed.

FIG. 3a illustrates another embodiment of a molecule sensor constructed in accordance with one or more embodiments of the present disclosure. In the embodiment of FIG. 3a, the structure includes a topological insulator 302 having multiple contacts 304 formed thereon.

Above the topological insulator 302, an insulating layer 305 is provided and a gate contact 310 is formed on at least a portion of the insulating layer 305. In some embodiments, the elements provided between the contacts 304 can be positioned in a trench 312 formed in the insulator 305. The embodiment of FIG. 3a also includes a hole 306 in contact 304, as discussed above with respect to FIG. 1.

FIG. 3b illustrates another embodiment of a molecule sensor constructed in accordance with one or more embodiments of the present disclosure. In the embodiment of FIG. 3b, the structure includes an insulator 301 having multiple contacts 304 formed thereon.

Between the contacts 304, a topological insulator layer 303 is formed and the topological insulator layer 303 is positioned over at least a portion of each of the contacts 304.

In some embodiments, an additional insulating layer can be formed between contacts. For example, in the embodiment of FIG. 3b, an insulating layer 305 is provided on topological insulator layer 303 with the gate contact 310 formed over the insulating layer 305.

Figure 4B:
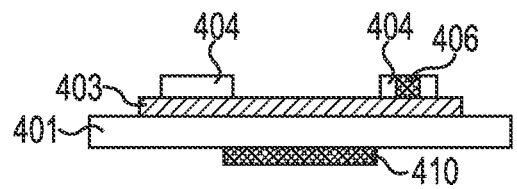

FIGS. 4a and 4b illustrate a side view of two embodiments of a molecule sensor constructed in accordance with one or more embodiments of the present disclosure. As shown in the embodiment of FIG. 4a, in some embodiments, the device can include an insulator 405 having metallic contacts 404 deposited thereon.

In some embodiments, the topological insulator layer (e.g., topological insulator 403 of FIG. 4b) can be a layer deposited on top of an insulator 401. In the embodiment shown in FIG. 4a, the topological insulator 402 is formed on top of at least a portion of one or both contacts 404. In some embodiments, the device (such as that shown in FIG. 2) can include a gate contact 410 on a back side of the insulator 401, as shown in FIGS. 4a and 4b.

As illustrated in the embodiments of FIGS. 4a and 4b, a topological insulator layer can be oriented either above or below the metallic contacts. If an insulator is used in addition to the topological insulator, such a structure can be accomplished by, for example, forming an insulator and forming the topological insulator layer on the insulator and wherein the metallic contacts are formed either on the insulator, with the topological insulator layer formed over at least a portion of the contacts, or on the topological insulator layer.

As discussed above, some embodiments can include a gate contact (e.g., electrode). In addition to those orientations illustrated in FIGS. 4a and 4b, as discussed above with respect to other embodiments of the present disclosure, the gate contact can also be formed between the contacts. FIG. 4b also includes a hole 406 which can be beneficial for the reasons discussed above, as well as other benefits.

In some such embodiments, an insulating layer can be formed on the gate contact. A topological insulator can also be formed between the contacts (e.g., on an insulating layer), in some such embodiments.

In various embodiments, an insulating layer can be formed between the contacts and a gate contact can be formed on the insulating layer. In some embodiments, the insulating layer can be formed on the topological insulator and the gate contact can be formed on the insulating layer. Some embodiments provide that a gate contact can be formed between the contacts, with an insulating layer formed on the gate contact, and a topological insulator formed between the contacts and on the insulating layer.

Figure 5:
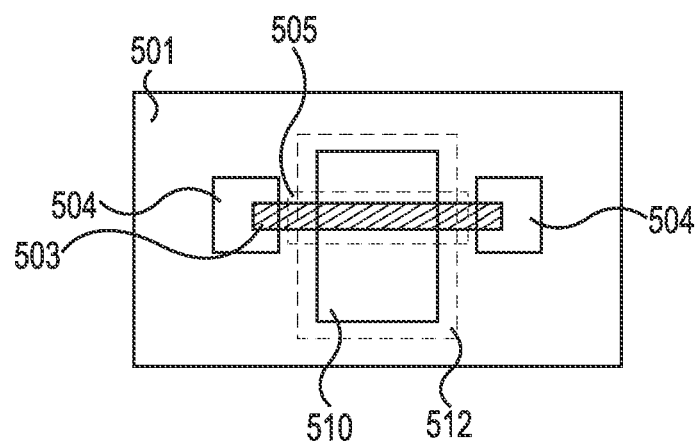
FIG. 5 illustrates another embodiment of a molecule sensor constructed in accordance with one or more embodiments of the present disclosure.

FIG. 5 illustrates another embodiment of a molecule sensor constructed in accordance with one or more embodiments of the present disclosure. In the embodiment of FIG. 5, the structure includes an insulator 501 having contacts 504 formed thereon.

The structure also includes a trench 512 formed between contacts 504. The trench has a gate contact 510 formed therein.

Also formed between the contacts 504 is an insulating layer 505. A topological insulator 503 is formed between the contacts 504 with a portion of the topological insulator 503 oriented on top of each contact 504.

In some embodiments, a gate contact can be grown between contacts that are pre-deposited on a substrate (e.g., insulator 501). Such a gate contact can be deposited directly on the insulator substrate or by providing a trench in the insulating substrate and forming the gate contact therein. In some such embodiments, an insulating layer can be formed over the gate contact. A topological insulator can be formed (e.g., grown or deposited) across the contacts, in some embodiments.

Any of the above structures can be utilized as a spectrometer (e.g., nanospectrometer) to investigate molecular vibration spectra, including the spectrum of a single molecule. Various embodiments provided herein can also be used as transistors.

The present disclosure also includes a number of method embodiments. For example, one method includes providing a topological insulator and metallic contacts either oriented above or below the topological insulator, applying a voltage across the contacts, measuring a current-voltage characteristic, measuring at least one or a first derivative and a second derivative of the current-voltage characteristic, and comparing a structure in one or more of the derivatives with a number of molecule vibration modes.

This comparison can, for example be accomplished by comparing the measured information with information stored in a database in the memory of a computing device. In such embodiments, the comparison could be accomplished by a user of the computing device or automatically, through us of a processor and/or other logic of a device. In some embodiments, the comparison could be accomplished by comparing the measured information with information stored in firmware or other logic circuitry.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A device for spectroscopic identification of molecules, comprising:
 a topological insulator layer oriented either above or below two metallic contacts;
 a hole, positioned in one of the contacts, such that the hole allows a molecule to pass through the contact and allows absorption of the molecule on the topological insulator; and
 wherein the contacts are oriented such that a voltage can be applied across the contacts and a current-voltage characteristic can be measured and compared to a number of molecule vibration modes.

2. The device of claim 1, wherein the device includes an insulator having the two metallic contacts deposited thereon.

3. The device of claim 2, wherein the device includes a gate contact on a back side of the insulator.

4. The device of claim 2, wherein the device provides that the topological insulator layer is formed on the insulator, an insulating layer is formed over at least a portion of the topological insulator, and a gate contact is formed over the insulating layer.

5. A method for spectroscopic identification of molecules, comprising:
 providing a topological insulator oriented either above or below two metallic contacts;
 providing a hole, positioned in one of the contacts, such that the hole allows a molecule to pass through the contact and allows absorption of the molecule on the topological insulator; and
 wherein the contacts are oriented such that a voltage can be applied across the contacts and a current-voltage characteristic can be measured and compared to a number of molecule vibration modes.

6. The method of claim 5, wherein the method includes forming the topological insulator between the two contacts.

7. The method of claim 5, wherein providing the topological insulator oriented either above or below the two metallic contacts is accomplished by forming an insulating layer and forming the topological insulator on the insulating layer and wherein the two metallic contacts are formed either on the insulating layer with the topological insulator formed over at least a portion of the contacts or on the topological insulator.

8. The method of claim 5, wherein the method includes:
forming an insulating layer between the two contacts; and
forming a gate contact on the insulating layer.

9. The method of claim 5, wherein the method includes:
forming an insulating layer on the topological insulator; and
forming a gate contact on the insulating layer.

10. The method of claim 5, wherein the method includes:
forming a gate contact on a back side of the insulating layer.

11. The method of claim 5, wherein the method includes:
forming a gate contact between the two contacts;
forming an insulating layer on the gate contact; and
forming a topological insulator between the two contacts, on the insulating layer.

12. The method of claim 5, wherein the method includes:
forming two contacts on the insulating layer; and
forming a topological insulator in a form of thin film, ribbon, nanoribbon, or nanowire, between the two contacts.

13. The method of claim 5, wherein:
forming the topological insulator on the insulating layer;
forming two contacts on the topological insulator; and
defining a hole in one of the contacts.

14. The method of claim 5, wherein the method includes:
forming an insulating layer between the two contacts; and
forming a gate contact on the insulating layer.

15. The method of claim 5, wherein the method includes:
forming an insulating layer on the topological insulator; and
forming a gate contact on the insulating layer.

16. The method of claim 7, wherein the method includes forming a gate contact on a back side of the insulator.

17. The method of the claim 7, wherein the method includes:
forming a gate contact between the two contacts;
forming the insulating layer on the gate contact; and
forming a topological insulator between the two contacts and above the insulating layer.

18. A method of spectroscopic identification of molecules, comprising:
providing a topological insulator and two metallic contacts either oriented above or below the topological insulator;
providing a hole, positioned in one of the contacts, such that the hole allows a molecule to pass through the contact and allows absorption of the molecule on the topological insulator;
applying a voltage across the contacts;
measuring a current-voltage characteristic;
measuring at least one of a first derivative and a second derivative of the current-voltage characteristic; and
comparing a structure in the current-voltage characteristic or in one or more of the derivatives with a number of molecule vibration modes.

* * * * *